United States Patent [19]

Shine

[11] 4,159,895
[45] Jul. 3, 1979

[54] METHOD AND APPARATUS FOR THE DETECTION OF BETA THALASSAEMIA MINOR

[75] Inventor: Ian B. Shine, Lexington, Ky.

[73] Assignee: Coulter Electronics, Inc., Hialeah, Fla.

[21] Appl. No.: 889,869

[22] Filed: Mar. 24, 1978

[30] Foreign Application Priority Data

Mar. 30, 1977 [GB] United Kingdom ............ 12779/77

[51] Int. Cl.² .......................................... G01N 33/16
[52] U.S. Cl. .................................. 23/230 B; 356/39; 356/40; 356/42; 364/416; 422/73
[58] Field of Search ............... 23/230 B, 259; 356/39, 356/40, 42; 424/11; 364/416; 422/73

[56] References Cited

U.S. PATENT DOCUMENTS

| | | | |
|---|---|---|---|
| 3,549,994 | 12/1970 | Rothermel | 356/39 X |
| 3,675,768 | 7/1972 | Legorreta-Sanchez | 356/39 X |
| 3,828,260 | 8/1974 | Underwood | 364/416 X |
| 3,923,397 | 12/1975 | Shuck | 356/39 |
| 4,030,888 | 6/1977 | Yamamoto | 356/39 X |
| 4,063,309 | 12/1977 | Hennessy | 364/416 X |
| 4,086,631 | 4/1978 | Vick | 364/416 |

OTHER PUBLICATIONS

Alvin H. Schmaier et al., Jour. of Pediatrics, 83(5), 794–797 (1973).
Chemical Abstracts, 80:25578j (1974).
Chemical Abstracts, 77:161639v (1972).
Chemical Abstracts, 85:59253t (1976).

*Primary Examiner*—Sidney Marantz
*Attorney, Agent, or Firm*—Coulter Electronics, Inc.

[57] ABSTRACT

Method and automatic, electronic apparatus for detecting carriers of thalassaemia, especially beta thalassaemia minor, which involve measuring the mean corpuscular volume (MCV) and the mean corpuscular hemoglobin (MCH) of a blood sample from the subject. A descriminant preferably defined as the product $(MCV)^2 MCH$, the thalassaemia index is obtained and compared with a predetermined thalassaemia index threshold value.

12 Claims, 5 Drawing Figures

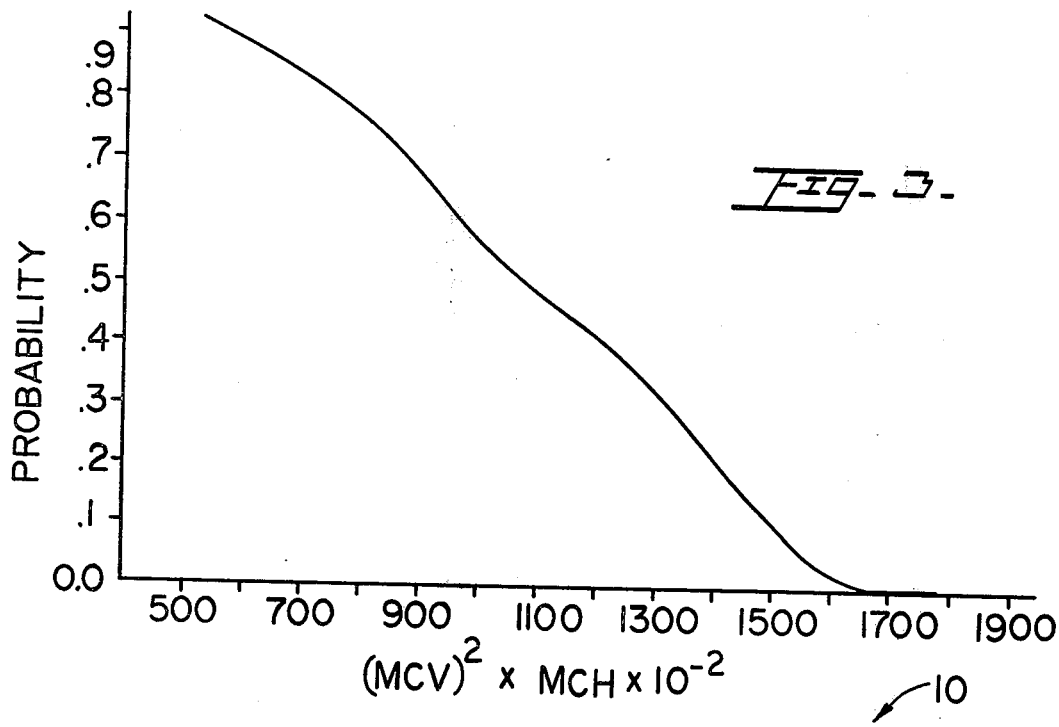
FIG. 3.
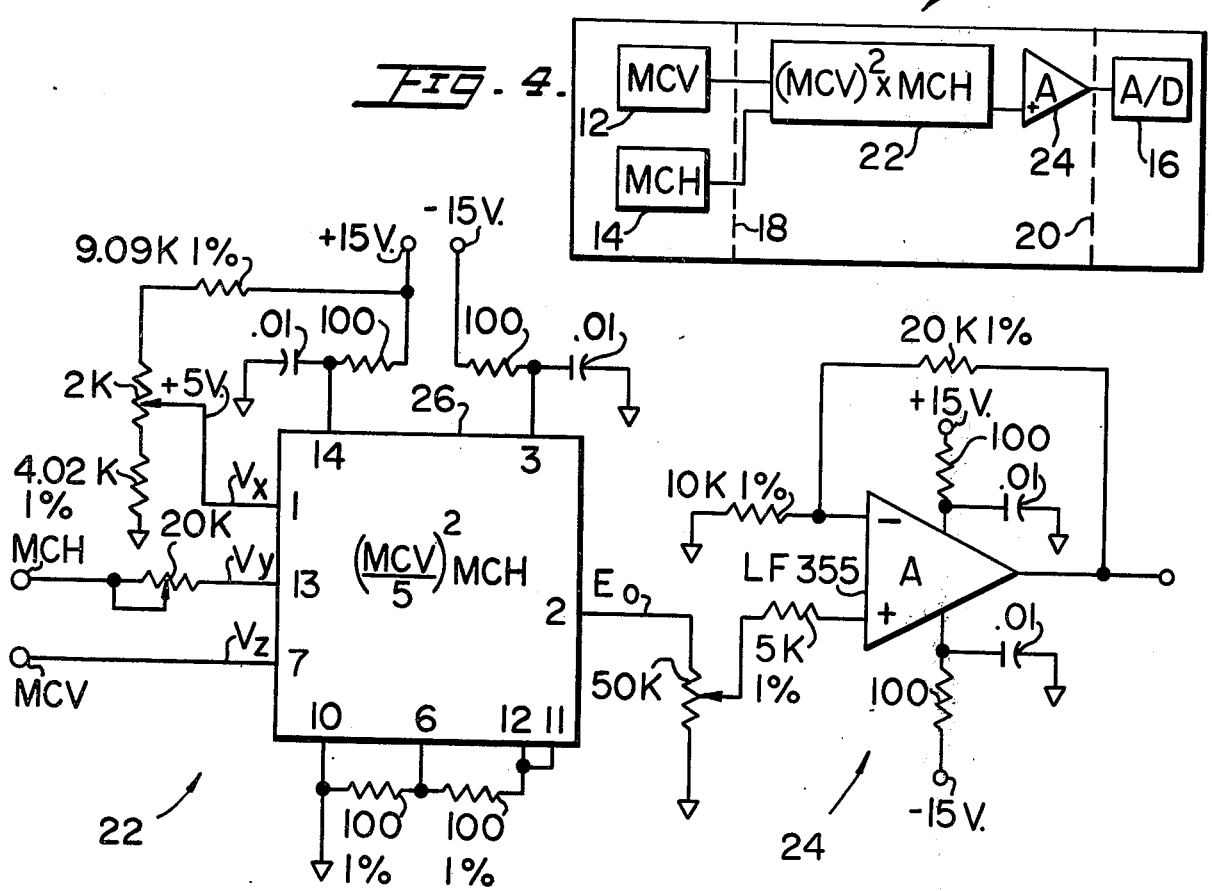
FIG. 4.
FIG. 5.

METHOD AND APPARATUS FOR THE DETECTION OF BETA THALASSAEMIA MINOR

BACKGROUND OF THE INVENTION

The present invention relates to the screening and detecting of blood disorders and more particularly to the screening and detecting of common thalassaemias and especially beta thalassaemia minor.

Currently in the United States many people are being offered education, testing, and genetic counselling for variant haemoglobins. It soon may be obligatory in the United States for physicians to inform patients of genetic risks, in which case, tests for variant haemoglobins should be able to screen detect thalassaemias and in particular beta thalassaemia minor.

The thalassaemias are a group of clinically important disorders caused by inherited defects in the rate of synthesis of normal haemoglobin. Beta thalassaemia minor is the most common of the thalassaemias and is the heterozygous expression of one of a set of genes, one of which produces no haemoglobin A, one of which interacts with beta chain variants producing a considerable amount of haemoglobin A but produces no increase in the RBC, and one of which has no haematological or clinical manifestations.

In the homozygous state, beta thalassaemia causes the death of about one hundred thousand children in the world per annum. It is thus desirable for there to be an accurate, yet relatively simple and inexpensive means to screen and detect the carriers of thalassaemias. As for any autosomal recessive disorder, theoretically the incidence of the homozygote could be reduced almost to zero if the heterozygote could be detected. An ideal test for the detection of heterozygotes should have no false negatives, few false positives and should be simple and reliable. Several tests in the past have been used, including measurement of osmotic fragility, fetal haemoblobin, free red cell porphyrin, blood smears, and haemoglobin $A_2$, yet none is readily adapted to mass screening. With the advent of electronic particle counters, estimates of red cell indices became more attractive and were combined or used singly to identify heterozygotes. As set forth herein, the three best methods were tested on 25,302 samples and all were found to miss known heterozygotes.

SUMMARY OF THE INVENTION

To overcome the insensitivity of the prior art, the preferred method and apparatus were developed to use the information already obtained from haemoglobin electrophoresis and extract the maximum information from the red blood cell indices.

The presently preferred method comprises three parts: (1) haemoglobin electrophoresis, (2) obtaining the product of the square of the mean corpuscular volume $(MCV)^2$ of the red blood cells multiplied by the means corpuscular haemoglobin (MCH) measured in units of one hundred, and (3) $A_2$ determination on all AA samples with $(MCV)^2 \times MCH < 1530$ and on those with variant genotypes consistent with thalassaemia.

Methods and apparatuses for accomplishing parts (1) and (3) are well known, but part (2), i.e., $(MCV)^2 \times MCH$, is believed to be new as part of a method for detection of thalassaemias, especially beta thalassaemia minor, and also new for use by itself as an indicator or screening index for thalassaemias and especially beta thalassaemia minor. I have found that the use of the product of $MCV \times MCH$ in lieu of $(MCV)^2 \times MCH$ is valuable as part (2) or by itself as an index, but not as accurate as $(MCV)^2 \times MCH$.

Methods and apparatuses measuring the separate parameters MCV and MCH also are well known. Disclosed herein is means for utilizing and adapting a well known apparatus, a Coulter Counter ® Model S particle analyzing device, to acquire automatically the value of $(MCV)^2 \times MCH$. The mark "Coulter Counter" is the Registered trademark, registration No. 679,591 of Coulter Electronics, Inc. of Hialeah, Florida.

BRIEF DESCRIPTION OF THE DRAWINGS

FIG. 3 is a probability curve having the $(MCV)^2 \times MCH$ thalassaemia index values along the abscissa and the beta thalassaemia minor probability values along the ordinate;

FIG. 4 is a block diagram of apparatus for obtaining the thalassaemia index values; and FIG. 5 is an electrical schematic drawing of a portion of the apparatus shown in FIG. 4.

DESCRIPTION OF THE PREFERRED EMBODIMENT

Figure 1:
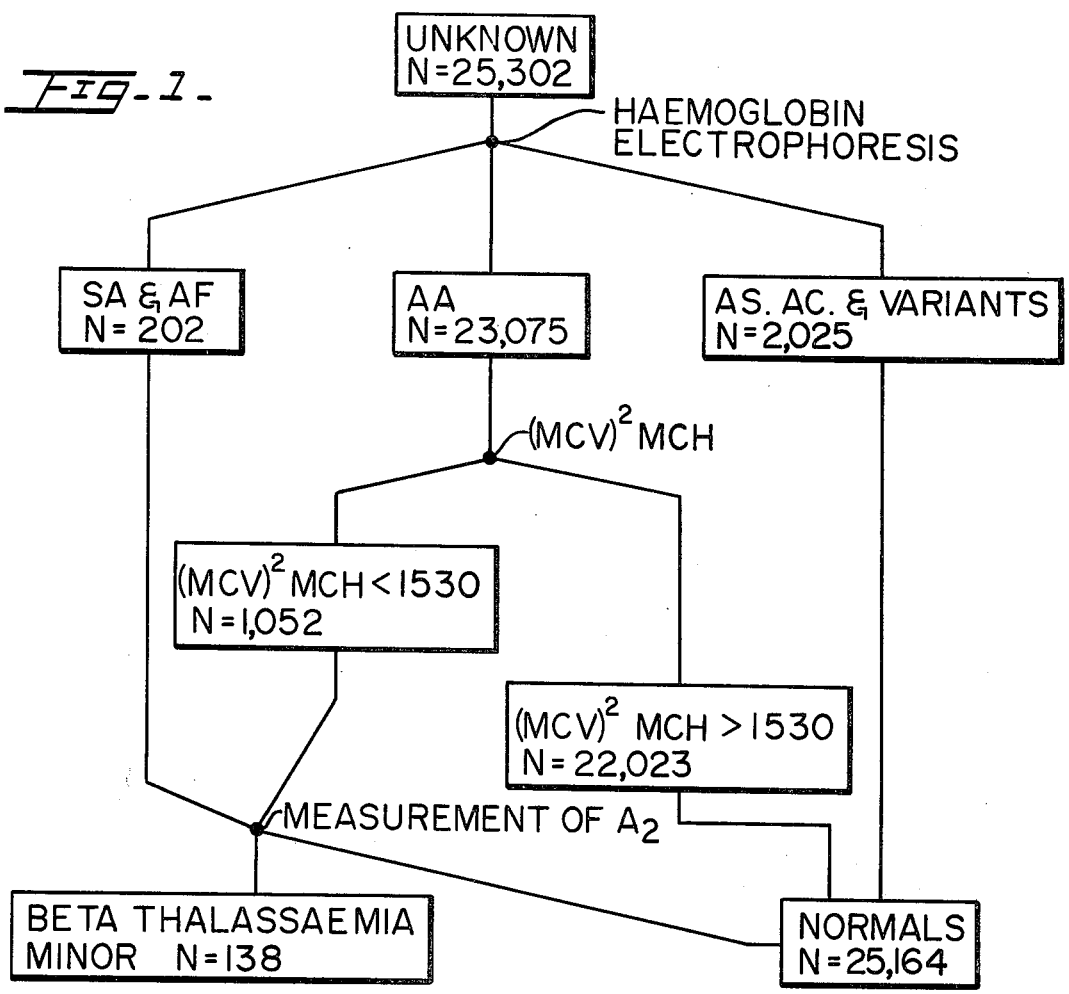
FIG. 1 is a chart showing the three parts of the preferred method and sample results obtained.

All three parts of the preferred method for detecting beta thalassaemia minor next will be disclosed, commencing with reference to the chart of FIG. 1. The results of this method have been highly satisfactory when compared to other well known methods. Such data is set forth in Table 1. This method of testing has led to a highly desirable means for screening thalassaemias, which means hereinafter will be called the "thalassaemia index" and resides in the determination of the red blood cell parameters MCV (mean cell or corpuscular volume) and MCH (mean corpuscular haemoglobin) and forming their mathematic product, preferably employing MCV raised to the power of two; i.e., $(MCV)^2 \times MCH$. The probability that a person is a carrier of thalassaemia is set forth in FIG. 3 and is increased the further his thalassaemia index is below a predetermined threshold value, as will be discussed subsequently.

Now, with reference to FIG. 1, a consecutive series of 25,302 healthy ambulant adult subjects were tested for inherited anaemias. 70.3% were Black and 29.7% were White of mixed North European ancestry with a small Mediterranean admixture. From each subject, a 5 ml sample of venous blood was drawn into a vacuum tube containing 7 mg EDTA. The haemoglobin type was identified in the well known manner by cellulose acetate electrophoresis with "tris" EDTA borate buffer at pH 8.4 and then by citrate agar electrophoresis in citrate buffer at pH 6.2 by Schneider's method. Whenever a band migrating as F was present, it was quantified by the known Betke technique. As samples were often one or two days old, red cells were not stained for fetal haemoglobin. Haemoglobin $A_2$ was measured in duplicate for all possibly thalassaemic samples, that is all samples with a mean corpuscular volume of less than 80 cubic microns, and on all with banding genotype AF, FA, or SA. Additionally, $A_2$ was measured on as many samples within the normal range as the daily work load would allow. Haemoglobin $A_2$ was separated from the whole blood on a DEAE cellulose minicolumn in glycine buffer and measured on a spectrophotometer at 415 nm. The measurement of $A_2$ was reproducible, except when the sample contained haemoglobin S. The extent of inaccuracy was measured on a pooled sample from 50 people with sickle-cell trait; the pooled "haemoglobin $A_2$" fraction was concentrated by dialysis and separated on a long column into 85.7% $A_2$ and 14.3% S. A model S Coulter Counter® calibrated daily against normal and abnormal controls was used to generate the red cell indices MCV, Hb, RBC and MCH. The indices were used to calculate the England and Fraser discriminant $(MCV-RBC-5Hb-3.4<1)$ to detect Pearson's threshold of MCV of less than 79 cubic microns and to calculate Mentzer's tentatively proposed ratio $(MCV/RBC<13)$.

The method of the preferred embodiment was developed heuristically to reduce the number of false positives and false negatives that occurred using other methods. The product of $(MCV)^2 \times MCH$ measured in units of 100 was calculated on each sample. Due to the known incompatibility of genotype AS with the diagnosis of beta thalassaemia minor, and the non-random distribution of genotypes among red cell indices, it was only necessary to use the product for samples with genotype AA, as is shown in FIG. 1 with respect to those 23,075 samples. Because males had 6.2% higher scores than females, all male scores were reduced by 6.2% to provide a uniform cut off point. Out of a total of 25,302 subjects tested, there were 138 identified with haemoglobin $A_2<4.5\%$. Four methods of detecting these 138 were compared as set forth in Table 1.

Figure 2:
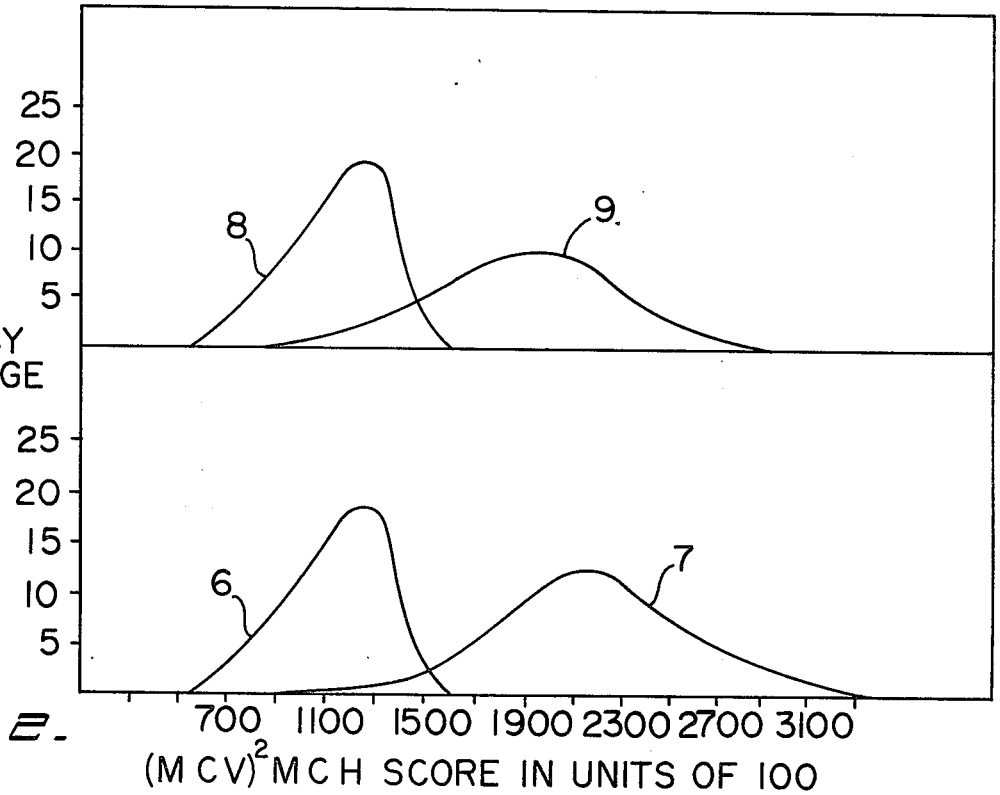
FIG. 2 contains two sets of distribution curves of $(MCV)^2 \times MCH$ in which beta thalassaemia minor is compared to normal and anaemic subjects.

The thalassaemia index $(MCV)^2 \times MCH$ values showed a wide separation between the thalassaemic and normal subjects, as is depicted in the lower half of FIG. 2 with respect to the thalassaemic curve 6 and the normal subject curve 7.

erozygotes for haemoglobins C and S tend to have thalassaemic red cells, and that the presence of SA or an increase of F in association with thalassaemia minor shifted the $(MCV)^2 \times MCH$ value into the normal range. This preferred embodiment missed only one heterozygotes, and produced only 4.4% false positives.

As more data becomes available from larger population studies, it may be found that the exponential value for MCV might best be at least slightly different than two. Hence, the power of two should not be narrowly understood, especially when interpreting the patent claims.

The measurement of haemoglobin $A_2$ has been considered the most reliable indicator of beta thalassaemia minor, although there is much variation between methods and between laboratories. Although 3.5% $A_2$ is the conventional threshold between beta thalassaemia minor and normal, in evaluating the effectiveness of the preferred method, the threshold was taken as 4.5%, because the intermediate range included several sample subjects for whom the diagnosis could not be supported clinically or genetically. Since the purpose of this study was to compare the value of different methods of detecting heterozygotes, it was decided to remove the intermediate range from consideration until genetic studies had been completed on everyone.

The $(MCV)^2 \times MCH$ thalassaemia index score also provides a measure of the likelihood that an individual is a heterozygote since the frequency of heterozygotes is generally inversely proportional to the score. The probability curve of FIG. 3 indicates a threshold value of 1530, below which a haemoglobin $A_2$ determination would be recommended. Below the value of 1530 lies 99% of the thalassaemic heterozygotes population and the range $<1530$ can be divided into subsets corresponding with different probabilities of this abnormality.

| METHOD | SAMPLES WITH $A_2 > 4.5\%$ | | | SAMPLES WITH $A_2 < 4.5\%$ | | |
|---|---|---|---|---|---|---|
| | DETECTED | MISSED | TOTAL | FALSE-POSITIVES | TRUE NEGATIVES | TOTAL |
| MCV²MCH | 137 (99.3%) | 1 (0.7%) | 138 | 1,116 (4.4%) | 24,048 (95.6%) | 25,164 |
| Pearson | 127 (92.0%) | 11 (8.0%) | 138 | 1,580 (6.3%) | 23,584 (93.7%) | 25,164 |
| Mentzer | 66 (47.8%) | 72 (52.2%) | 138 | 171 (0.7%) | 24,993 (99.3%) | 25,164 |
| England & Fraser | 76 (55.1%) | 62 (44.9%) | 138 | 645 (2.6%) | 24,519 (97.4%) | 25,164 |

The mean score for the thalassaemics was 1,094 ±259; and the mean score for the AA non-thalassaemics was 2,218 ±386. This difference was highly significant, $t=20.5$, $p<0.0001$. The single person who was missed had haematological values within normal limits, and would elude detection by any method based on red cell indices. Similar carriers with normal haematological values are probably quite rare, since none were found among 1,761 people with microcytosis for whom $A_2$ was measured and only one example was found among 1,973 people without microcytosis for whom $A_2$ was measured. The thalassaemia index values also effected a wide separation between the means of heterozygotes 1,094 ±259 and anaemic people 1,814 ±601, respectively in curves 8 and 9 shown in the upper half of FIG. 2, defining anaemia as a haemoglobin concentration below 12 g/dl in males and below 11 g/dl in females, $t=7.7$, $p<0.0001$.

Experimentation with the use of the red blood cell indices MCV and MCH has shown that their product does provide an informative thalassaemia index (data is not set forth herein), but that the use of $(MCV)^2$ results in more informative results. It was discovered that het- The apparatus 10 shown in block form in FIG. 4 can be employed for obtaining the thalassaemia index. The MCV, MCH and A/D blocks 12, 14 and 16 represent existing portions of a Coulter Counter® Model S particle analyzer, but are not restrictive to that product. The dashed lines 18 and 20 depict the fact that the blocks therebetween are all that which would be needed to be added to the Model S to enable it to provide the thalassaemia index. The analogue outputs of MCV and MCH are fed to the function block 22 which yields the analogue value of $(MCV)^2 \times MCH$. So that this analogue value of the thalassaemia index can be converted into a digital value by the already existing analogue to digital converter block 16, there is provided an amplifier 24 which has the purpose of providing a scale factor.

FIG. 5 shows the schematic details of the blocks 22 and 24. The primary component of the function block 22 is a function converter 26, a commercial version of which is manufactured by Burr-Brown Research Corporation, Tucson, Arizona, as product number 4302. Of course, the desired funtion $(MCV)^2 \times MCH$ can be obtained by suitable alternate circuitry. The $V_x$ input is a scaling input and is chosen as $+5V$ to bring the operation of the analogue function within the operating range of the Model S. The 50 K resistor is coupled to the output $E_o$ to provide a calibration factor for the A/D converter 24. Connected as shown in FIGS. 4 and 5, the digital value of the thalassaemia index can be derived by and printed out by a Model S.

Information concerning the construction and operation of a Model S particle analyzer can be obtained from U.S. Pat. No. 3,549,994, which has equivalents in many foreign countries. As mentioned in the patent and as is well known, MCV can be derived as the quotient of hematocrit and red blood cell count, i.e., MCV=HCT/RBC; and also, MCH is the quotient of haemoglobin and red blood cell count, i.e., MCH=Hb/RBC. All of these blood parameters are obtained by a Model S. However, it will be appreciated that neither the analogue nor the numerical values of MCV and MCH need be obtained and only their equivalents HCT/RBC and Hb/RBC are necessary and those can be obtained in either an analogue or digital form, depending upon a wide choice of known methods and apparatuses.

The thalassaemia index also provides a highly informative discriminant between sickle cell anaemia and sickel cell beta thalassaemia, such two conditions having very different prognoses, but yet frequently being confused during diagnosis. I have ascertained that the mean thalassaemia index score for sickle cell beta thalassaemia approximates 1000, and that the mean index score for sickle cell anaemia approximates 2700.

It is believed the foregoing will enable those skilled in the art to understand and practice the invention, both method and apparatus, and, to the extent as may become desired or required, deviate from some of the details hereinabove set forth, but still remaining within the scope and spirit of the invention as claimed herein.

What I seek to be protected by United States Letter Patent is:

1. A method for detecting carriers of thalassaemias, especially beta thalassaemia minor, comprising the steps of: obtaining from a blood sample the measurements of mean corpuscular volume of the red blood cells and the mean corpuscular haemoglobin; developing as a thalassaemia index value the mathematic product of said two parameter measurements; and comparing said product with a predetermined thalassaemia index threshold value, the amount that the thalassaemia index value is less than the threshold value being proportional to the probability that the sample is from a thalassaemia carrier.

2. A method according to claim 1 including the step of conducting an $A_2$ determination upon at least those samples having thalassaemia index values below said threshold value.

3. A method according to claim 1 in which the predetermined threshold value approximates 1530.

4. A method according to claim 1 in which samples from males have their thalassaemia index values reduced by approximately 6.2% before said comparing.

5. A method according to claim 1 in which, in developing said thalassaemia index, it is the square of the mean corpuscular volume that forms a product with the mean corpuscular haemoglobin.

6. A method according to claim 1 in which the blood samples undergo haemoglobin electrophoresis and only samples with genotype AA are subjected to said steps of developing and comparing.

7. A method according to claim 6 including the step of conducting an $A_2$ determination upon at least those samples having thalassaemia index values below said threshold valve.

8. A method according to claim 7 in which, in developing said thalassaemia index, it is the square of the mean corpuscular volume that forms a product with the mean corpuscular haemoglobin.

9. A method according to claim 8 in which the pretermined threshold value approximates 1530.

10. Apparatus for use in detecting carriers of thalassaemias, especially beta thalassaemia minor, said apparatus comprising: means for obtaining from a blood sample the measurements of the parameters of the mean corpuscular volume of the red blood cells and the mean corpuscular haemoglobin; means for developing as a thalassaemia index value the mathematic product of the two parameter measurements; and means for presenting the developed thalassaemia index value so that it can be compared with at least one predetermined standard thalassaemia index value, whereby the probability of the sample being from a carrier of thalassaemia can be ascertained.

11. Apparatus according to claim 10 in which said developing means generates as the thalassaemia index the value $(MCV)^2 \times MCH$.

12. Apparatus according to claim 10 in which at least said measurement obtaining means and preferably also said thalassaemia index developing means and said presenting means are parts of an automatic blood cell analyzing device.

* * * * *